(12) United States Patent
Palmer (10) Patent No.: US 9,782,563 B2
(45) Date of Patent: Oct. 10, 2017

(54) CATHETER PACKAGING WITH MOVEMENT CONTROL DEVICE

(71) Applicant: CURE MEDICAL, LLC, Newport Beach, CA (US)

(72) Inventor: Timothy Palmer, Marine on St. Croix, MN (US)

(73) Assignee: CURE MEDICAL, LLC, Newport Beach, CA (US)

( * ) Notice: Subject to any disclaimer, the term of this patent is extended or adjusted under 35 U.S.C. 154(b) by 392 days.

(21) Appl. No.: 14/296,995

(22) Filed: Jun. 5, 2014

(65) Prior Publication Data

US 2015/0352324 A1 Dec. 10, 2015

(51) Int. Cl.
| | | |
|---|---|---|
| *A61M 25/00* | (2006.01) | |
| *A61M 25/01* | (2006.01) | |
| *F16B 2/24* | (2006.01) | |
| *F16M 11/04* | (2006.01) | |

(52) U.S. Cl.
CPC ....... *A61M 25/0111* (2013.01); *A61M 25/002* (2013.01); *A61M 25/0017* (2013.01); *A61M 2202/0014* (2013.01); *A61M 2202/0496* (2013.01); *A61M 2209/06* (2013.01); *F16B 2/246* (2013.01); *F16M 11/041* (2013.01); *F16M 2200/027* (2013.01)

(58) Field of Classification Search
CPC .. A61M 2202/0014; A61M 2202/0496; A61M 2209/06; A61M 25/0017; A61M 25/002; A61M 25/0111; A61M 25/013; A61M 2210/1085; A61M 2210/1089; A61M 25/0113; A61F 5/44; A61F 2002/9517; A47L 13/512; B25H 3/04; Y10T 403/595; F16B 2/246; F16M 2200/027; F16M 11/041; A61B 1/00147; A61B 1/0014; A61B 1/00135; A61B 1/00131; A61B 17/3498; A61B 17/3494; A61B 17/3496
See application file for complete search history.

(56) References Cited

U.S. PATENT DOCUMENTS

| | | | | | |
|---|---|---|---|---|---|
| 836,303 | A | * | 11/1906 | Christensen | ............ E21B 19/10 108/148 |
| 1,206,655 | A | * | 11/1916 | Belcher | ................. A47L 13/512 211/66 |
| 2,131,956 | A | * | 10/1938 | Jones | .................... A47L 13/512 248/113 |
| 2,221,801 | A | * | 11/1940 | Keppinger | ............ A47L 13/512 131/257 |

(Continued)

*Primary Examiner* — Adam Marcetich
(74) *Attorney, Agent, or Firm* — Sherrill Law Offices, PLLC (57) ABSTRACT

A packaged intermittent urinary catheter having a longitudinally extending package and a catheter movement control device. The catheter movement control device is disposed within the package and has a monolithic planar locking member and a one-way valve. The monolithic locking member has longitudinally spaced upper and lower surfaces, laterally spaced ends, and transversely spaced front and back edges. The valve is disposed through the upper and lower surfaces of the locking member and configured and arranged for receipt of the catheter tube and to advance the tube through the locking member in the first longitudinal direction only.

6 Claims, 8 Drawing Sheets

(56) References Cited

U.S. PATENT DOCUMENTS

| | | | | |
|---|---|---|---|---|
| 2,422,891 A | * | 6/1947 | Dickson | A47L 13/512 |
| | | | | 211/65 |
| 2,584,644 A | * | 2/1952 | Verdi | A47L 13/512 |
| | | | | 211/105.1 |
| 2,894,119 A | * | 7/1959 | Stenger | F21L 15/08 |
| | | | | 224/249 |
| 3,365,761 A | * | 1/1968 | Kalvig | B25H 3/04 |
| | | | | 211/65 |
| 4,141,452 A | * | 2/1979 | Martin | A47L 13/512 |
| | | | | 211/66 |
| 4,230,115 A | | 10/1980 | Walz, Jr. et al. | |
| 5,108,066 A | * | 4/1992 | Lundstrom | A63B 21/0728 |
| | | | | 24/524 |
| 5,224,681 A | * | 7/1993 | Lundstrom | F16B 2/246 |
| | | | | 24/522 |
| D358,679 S | * | 5/1995 | Garrity | D26/138 |
| 5,454,798 A | | 10/1995 | Kubalak et al. | |
| 5,529,148 A | * | 6/1996 | O'Leary | E05C 17/30 |
| | | | | 16/49 |
| 5,603,702 A | * | 2/1997 | Smith | A61B 17/3462 |
| | | | | 251/149.1 |
| 5,690,645 A | * | 11/1997 | Van Erp | A61M 25/0113 |
| | | | | 604/116 |
| 5,993,437 A | * | 11/1999 | Raoz | A61M 39/12 |
| | | | | 128/912 |
| 6,010,105 A | * | 1/2000 | Davis | A47L 13/512 |
| | | | | 211/113 |
| 6,053,905 A | | 4/2000 | Daignault, Jr. et al. | |
| 6,179,514 B1 | * | 1/2001 | Cheng | B25G 3/10 |
| | | | | 285/308 |
| 6,402,726 B1 | | 6/2002 | Genese | |
| 6,427,964 B1 | * | 8/2002 | Hillstrom | G09F 15/0062 |
| | | | | 248/314 |
| 6,578,709 B1 | | 6/2003 | Kavanagh et al. | |
| 7,458,964 B2 | | 12/2008 | Mosler et al. | |
| 2003/0050653 A1 | * | 3/2003 | Berger | A61B 17/34 |
| | | | | 606/151 |
| 2007/0073222 A1 | * | 3/2007 | Lilley | A61M 25/0618 |
| | | | | 604/110 |
| 2008/0103464 A1 | * | 5/2008 | Mosler | A61M 25/013 |
| | | | | 604/349 |

* cited by examiner

CATHETER PACKAGING WITH MOVEMENT CONTROL DEVICE

BACKGROUND

Intermittent catheters are typically used by patients suffering from urinary incontinence or by individuals unable to have voluntary urination. In our highly mobile culture, the ability to have the freedom to leave home for the day or longer is an important part of life. To accommodate this need single use catheters have been developed to allow patients to perform self catheterization. To aid in the insertion of the catheter in a body cavity they are often lubricated making the handling of the catheter difficult and messy. Many catheter packages are now designed to aid in the use of the catheter and at least the funnel end of the catheter is retained in the package. This allows the user to use the package to manipulate the catheter and avoid the messy and possible insanitary handling of the actual catheter. Manipulating a slippery catheter through a plastic bag can be quite difficult even for someone with excellent dexterity. To aid in the manipulation of the catheter various devices have been conceived to limit or control the movement of the catheter into and out of its package.

Many of these movement control devices have multiple parts increasing cost, weight, and waste of the overall catheter and packaging.

Therefore, a need exists for a low cost, lightweight, and low waste catheter movement control device.

SUMMARY OF THE INVENTION

The invention is an intermittent urinary catheter packaging having a longitudinally extending package and a catheter movement control device. The catheter movement control device is disposed within the package and has a monolithic planar locking member and a one-way valve. The monolithic locking member has longitudinally spaced upper and lower surfaces, laterally spaced ends, and transversely spaced front and back edges. The valve is disposed through the upper and lower surfaces of the locking member and configured and arranged for receipt of the catheter tube and to advance the tube through the locking member in the first longitudinal direction only.

DETAILED DESCRIPTION OF A PREFERRED EMBODIMENT

Nomenclature

- 10 Catheter packaging
- 20 Package
- 21 Longitudinally extending side
- 22 Exit
- 23 First longitudinal end
- 24 Second longitudinal end
- 25 Receiving chamber
- 26 Line of weakness
- 30 Movement control device
- 40 Monolithic planar locking member
- 41a Upper surface
- 41b Lower surface
- 42 Lateral end
- 43a Front edge
- 43b Back edge
- 44 Locking orifice
- 45 Snap fit latch
- 50 Valve
- 60 Housing
- 61 Longitudinal axis
- 62 Pathway
- 63 First longitudinally extending engagement member
- 64 Second longitudinally extending engagement member
- 65 Slots or catches
- 66 First longitudinal end
- 67 Second longitudinal end
- 68 Cap or seal
- 70 Catheter
- 71 Lumen end
- 72 Funnel end
- 80 Lubricant
- X1 First longitudinal direction
- X2 Second longitudinal direction
- Y Lateral direction
- Z Transverse direction

DESCRIPTION

Construction

The invention is catheter packaging 10 with a package 20 and a catheter movement control device 30. The package 20 has a first longitudinal end 23 and a second longitudinal end 24 and defines a longitudinally elongate catheter receiving chamber 25 extending along a portion of the full longitudinal length of the package 20 configured to contain at least part of a catheter 70. Preferably the entire catheter 70 is carried in the elongate receiving chamber 25 with the lumen end 71 of the catheter 70 located proximate the first longitudinal end 23 of the package 20 and the funnel end 72 proximate the second longitudinal end 24 of the package 20.

Figure 1:
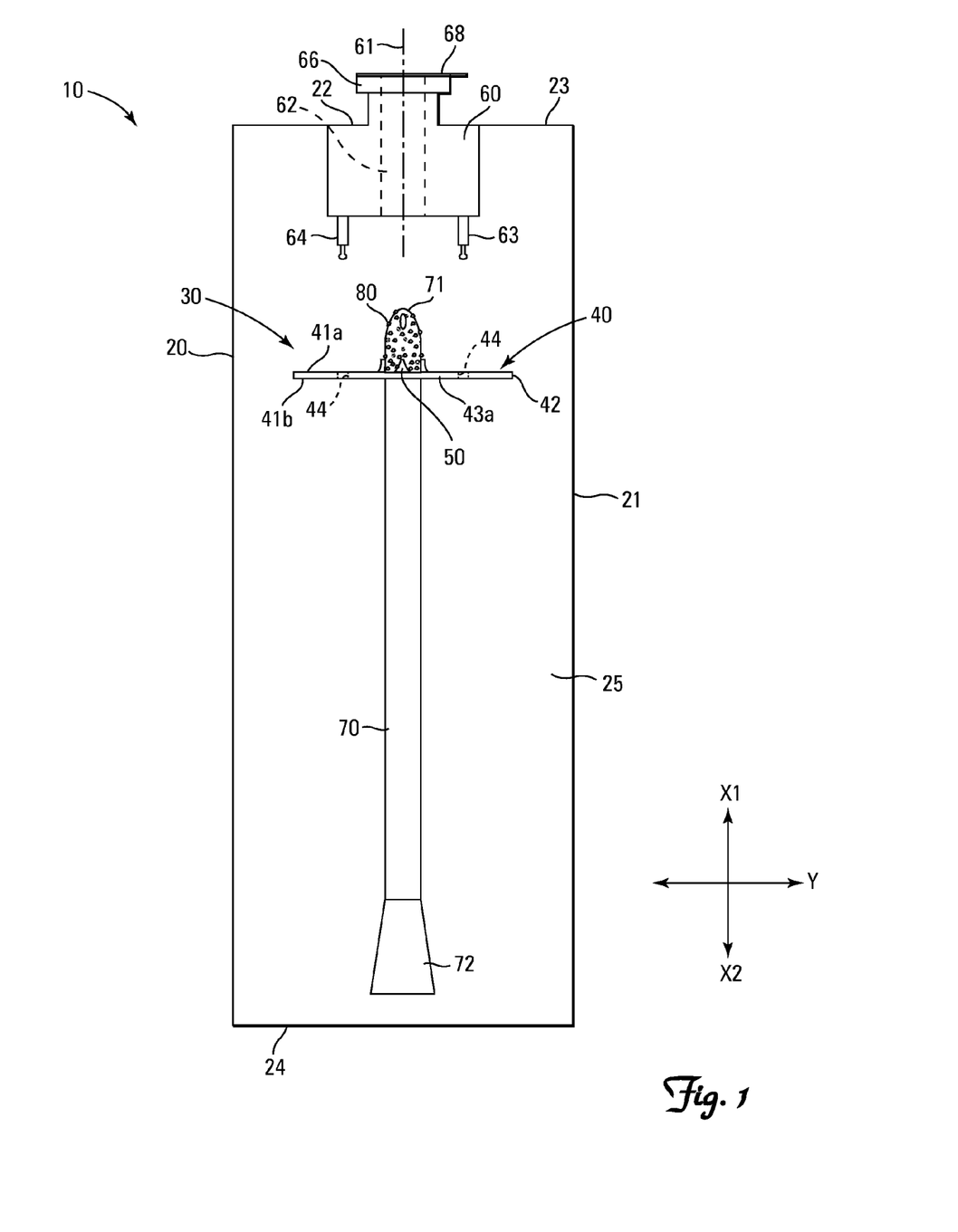
FIG. 1 is a front plan view of the invention with a first embodiment of the movement control device.

As shown in FIG. 1, a preferred embodiment of the package 20 may be constructed from a base sheet of material and cover sheet of material sealed along the edges to form the catheter receiving chamber 25 therein. The first longitudinal end 23 and the second longitudinal end 24 are sealed after insertion of the catheter 70 and movement control device 30 in the receiving chamber 25. A second embodiment of the package 20 may also be constructed from a single base material folded upon it to provide a single sealed longitudinal edge. The first longitudinal end 23 and second longitudinal end 24 are then sealed after insertion of the catheter 70 and movement control device 30 in the receiving chamber 25. In a third embodiment the package 20 may be extruded in a tube shape and then the first longitudinal end 23 and second longitudinal end 24 sealed after insertion of the catheter 70 and movement control device 30 in the receiving chamber 25.

The catheter 70 inserted in the package 20 is an intermittent catheter 70. The catheter 70 may be coated with a hydrophilic coating to provide a low friction surface when treated with a swelling medium. A swelling medium may be provided within the package 20 to provide a ready to use catheter 70. A lubricant 80 may also be provided in the package 20 to provide a low friction surface.

The catheter 70 may have any desired longitudinal length and shape effective for achieving the function of eliminating urine from the bladder of a male or female patient. Preferably, the longitudinal length for an adult female catheter 70 is between 2-6 inches, the longitudinal length of the adult male catheter 70 is between 10-16 inches, and the longitudinal length of a pediatric catheter 70 is between 5-11 inches.

The catheter receiving chamber 25 also contains within it a catheter movement control device 30. The catheter movement control device 30 has a monolithic planar locking member 40 and a one-way valve 50. The locking member 40 has longitudinally spaced upper and lower surfaces 41a and 41b, laterally spaced ends 42, and transversely spaced front and back edges 43a and 43b. The locking member 40 may be made from any suitable thin and lightweight material. Preferably the locking member 40 is made of a heavy flexible polyvinyl chloride (PVC) film.

The locking member 40 has a one-way valve 50 disposed through the upper and lower surfaces 41a and 41b of the locking member 40 as shown in FIGS. 1, 4, 6A, and 9 to allow movement of the catheter 70 through the locking member 40 in the first longitudinal direction X1 but not the second longitudinal direction X2. Any type of one way valve 50 may be utilized. Preferably a tricuspid or quadricuspid valve 50 is used. The valve 50 is sized and shaped to allow the catheter 70 to move freely through the locking member 40 in the first longitudinal direction X1 and not the second longitudinal direction X2.

The catheter movement control device 30 may also have a catheter housing 60. The housing 60 has a first longitudinal end 66 and a second longitudinal end 67. Preferably the housing 60 is attached to at least one of the longitudinally extending sides 21 of the package 20. Most preferably the housing 60 is positioned within the exit 22 to the package 20 as shown in FIG. 1 with the first longitudinal end 66 of the housing 60 allowing the catheter 70 to exit from the package 20 and the second longitudinal end 67 of the housing 60 within the receiving chamber 25. The housing 60 has a longitudinal axis 61 and defines a longitudinally extending pathway 62 through the housing 60. The pathway 62 is sized and configured for receipt of the catheter 70. The housing 60 is disposed a longitudinal distance from the valve 50 in the first longitudinal direction X1. The housing 60 may also be disposed a longitudinal distance for the first longitudinal end 23 of the package 20.

Figure 5:
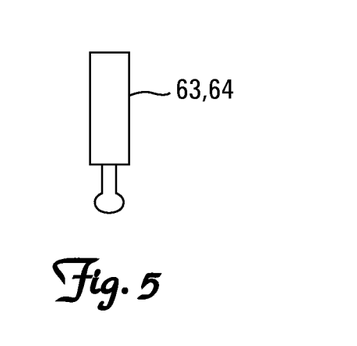
FIG. 5 is an enlarged front plan view of the longitudinally extending posts shown in FIG. 3.

In a second embodiment of the housing 60, the housing 60 has one or two longitudinally extending and laterally spaced engagement members 63 and 64 extending in the second longitudinal direction X2 from the second longitudinal end 67 of the housing 60. See FIGS. 1-3. The engagement member may be any shape and size to allow engagement with corresponding locking orifices 44 disposed through the upper and lower surfaces 41a and 41b of the locking member 40 shown in FIG. 4. Preferably the engagement members 63 and 64 are post shaped members 63 and 64 as shown in FIG. 5. Preferably the housing 60 is made from a lightweight plastic.

Figure 7:
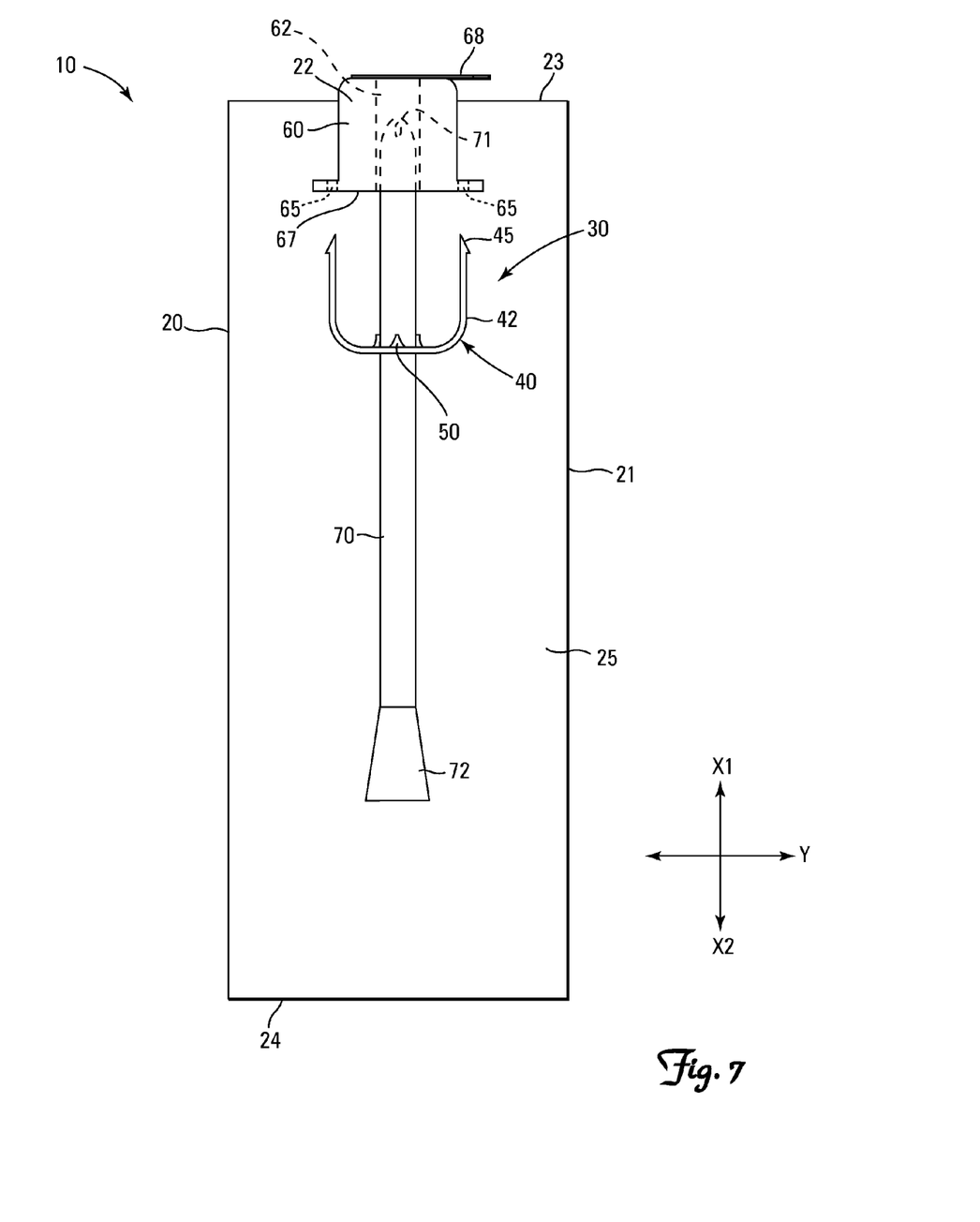
FIG. 7 is a front plan view of a third embodiment of the catheter movement control device in the package.
Figure 8:
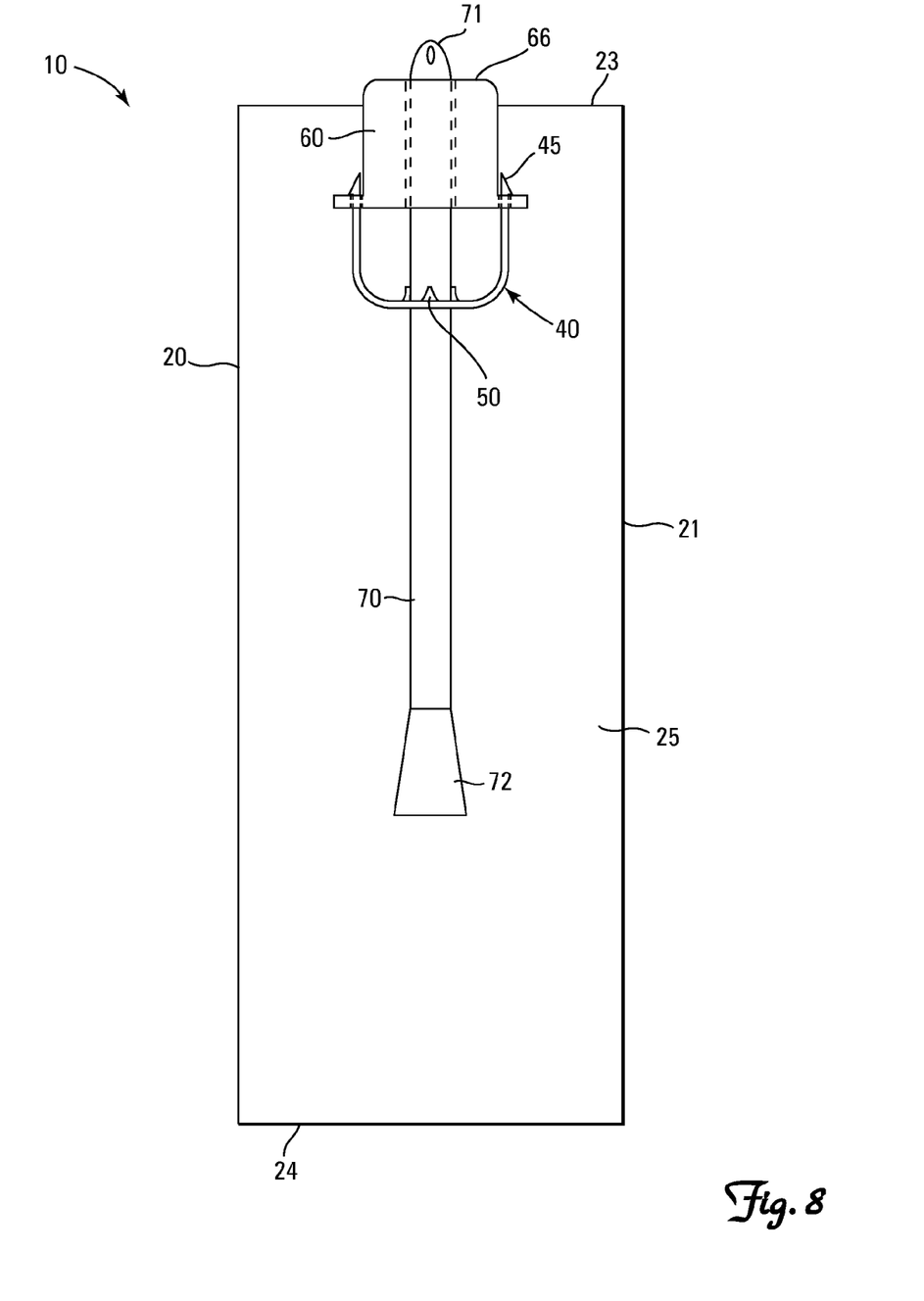
FIG. 8 is a front plan view of the catheter movement control device in FIG. 7 with the movement control device engaging the housing to prevent movement in the second longitudinal direction.

In a third embodiment of the housing 60, the housing 60 has two laterally spaced slots or catches 65 in the second longitudinal end 67 configured and arranged to snap fit with the locking member 40. In this embodiment the locking member 40 has a snap fit latch 45 extending in the first longitudinal direction X1 on the first and second lateral ends 42 as shown in FIGS. 7 and 8. The snap fit latches 45 are configured and arranged to deflect and snap into the slot or catch 65 of the housing 60 to prevent movement of the locking member 40 in the second longitudinal direction X2.

Figure 6:
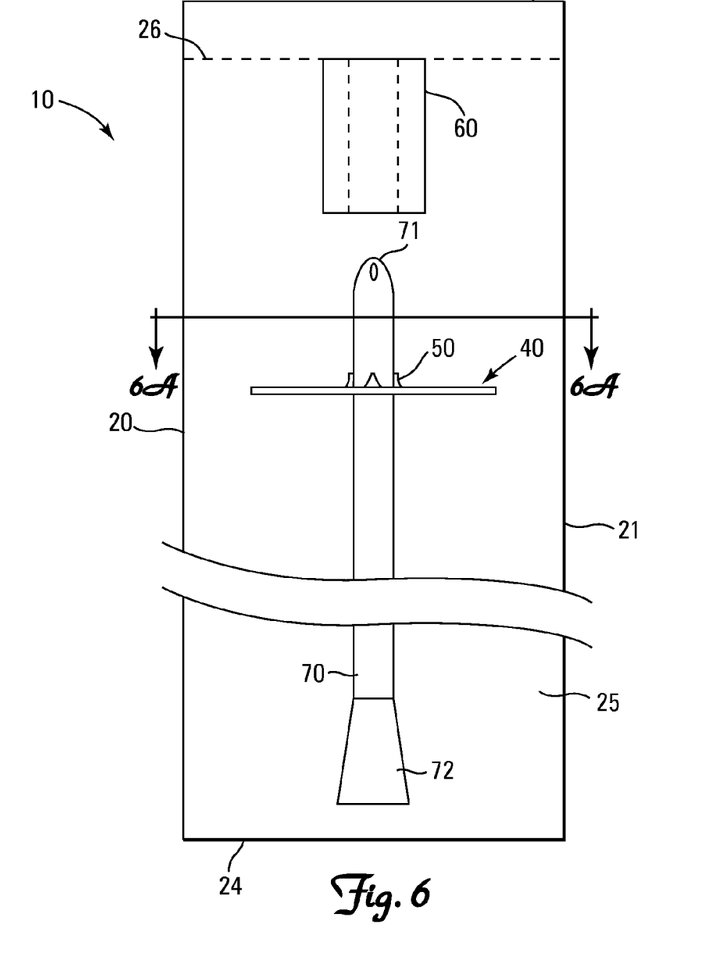
FIG. 6 is a front plan view of a second embodiment of the movement control device.
Figure 6A:
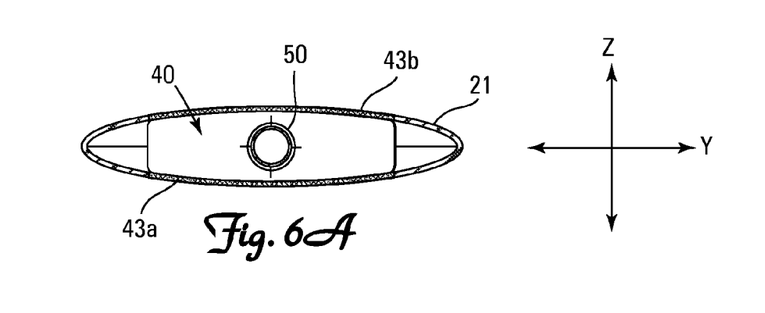
FIG. 6a is top view of the catheter movement control device along the line A-A of FIG. 6 wherein the transversely spaced front and back edges are attached to the longitudinal sides of the package.
Figure 9:
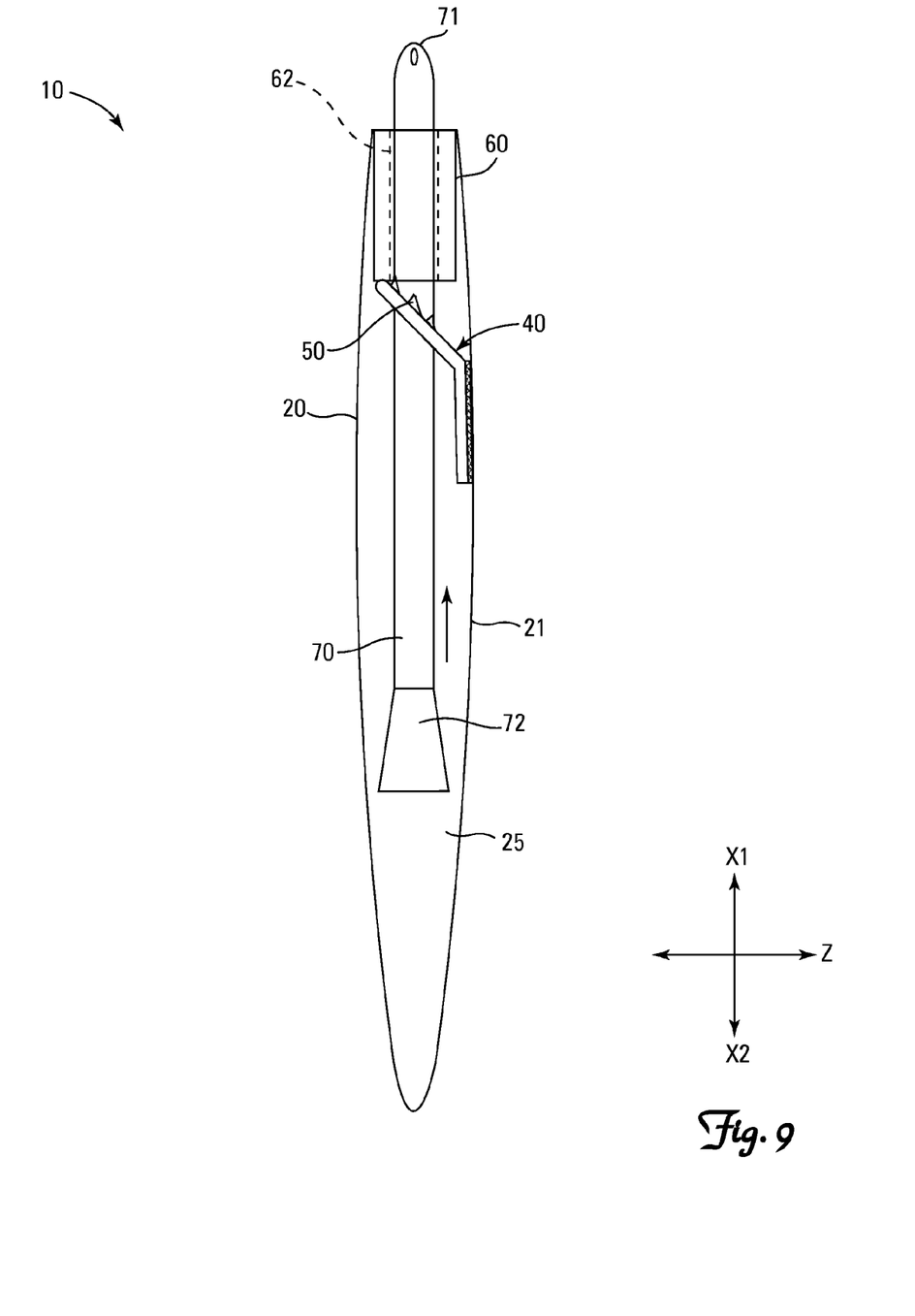
FIG. 9 is a side plan view of a fourth embodiment of the catheter movement control device with a back edge hingedly attached to a longitudinal side of the package.

The monolithic planar locking member 40 may also be attached to a longitudinally extending side 21 of the package 20. Either the lateral ends 42 or the front and back edges 43a and 43b can be attached to the package 20. As shown in FIGS. 6 and 6A, the transversely spaced front and back edges 43a and 43b of the locking member 40 may be welded to the package 20 to prevent the locking member 40 from moving in the longitudinal direction relative to the package 20. As shown in FIG. 9, either the front edge 43a or back edge 43b may be hingedly attached to the package 20.

Use

The packaged intermittent urinary catheter 10 is used by patients for self catheterization. Prior to use the patient should take all sanitary procedures advised by their doctors to decrease the risks of infection from utilizing a catheter 10.

No Housing

In the embodiment of the invention shown in FIG. 6, the package 20 has no housing 60 at the first longitudinal end 23. To open the package 20 to access the catheter 70, the patient grasps the first longitudinal end 23 of the package 20 and removes the end 23. The end 23 may be removed by cutting with a knife or scissors, but preferably the end 23 is removed manually along a line of weakness 26. By removing the first longitudinal end 23 at the point of weakness or line of weakness 26, the package 20 will open such that the receiving chamber 25 is now open.

The second longitudinal end 24 of the package 20 may also be removed to allow the package 20 to be used as an extended drainage tube or left intact so that the package 20 can be used as collection vessel. The second longitudinal end 24 may be removed by cutting with a knife or scissors, but preferably the end 24 is removed manually along a line or point of weakness 26.

Both the front edge 43a and back edge 43b of the locking member 40 are attached or fused to the longitudinally extending sides 21 of the package 20 preventing any longitudinal movement of the locking member 40. The user grasps the catheter 70 below the locking member 40 (near the funnel end 72) and urges the catheter 70 in the first longitudinal direction X1 through the locking member 40 until the lumen end 71 of the catheter 70 advances out of the package 20. The catheter 70 continues to be advanced out of the package 20 and into the urethra of the user. If the catheter 70 encounters resistance advancing in the first longitudinal direction X1, the one-way valve 50 in the locking member 40 grabs the catheter 70 and prevents it from moving in the second longitudinal direction X2.

Housing

If the package 20 has a housing 60 located within the exit 22 of the package 20, a seal or cap 68 covers the opening out of the housing 60. See FIGS. 1, 2 and 7. The seal or cap 68 is removed to open the pathway 62 through the housing 60 and catheter receiving chamber 25.

Locking Member Attached to Package

In the embodiment of the invention shown in FIG. 9, the movement control device 30 includes a housing 60. Only one edge of the locking member 40 is attached to a longitudinally extending side 21 of the package 20. Preferably this attached edge is hingedly attached. This allows the other edge to move in both the first longitudinal direction X1 and the second longitudinal direction X2. The user grasps the catheter 70 below the locking member 40 (near the funnel end 72) and urges the catheter 70 in the first longitudinal direction X1 through the locking member 40 until the lumen end 71 of the catheter 70 advances out of the package 20. The catheter 70 continues to be advanced through the pathway 62 of the housing 60 and out of the package 20 and into the urethra of the user. If the catheter 70 encounters resistance advancing in the first longitudinal direction X1, the one-way valve 50 in the locking member 40 grabs the catheter 70 and prevents it from moving in the second longitudinal direction X2. As the catheter 70 is advanced, the unattached edge of the locking member 40 moves with the catheter 70 until it comes into contact with the housing 60. This contact prevents the unattached edge of the locking member 40 from continuing to advance in the first direction and preventing movement in the first longitudinal direction X1 of the catheter 70 through the one way valve 50. The lumen end 71 of the catheter 70 is advanced through the pathway 62 through the housing 60 and out of the package 20.

Locking Member Attached to Housing

In the embodiment of the invention shown in FIGS. 1-3 and 7-8 the user grasps the catheter 70 through the package 20 below the locking member 40 and manually urges the catheter 70 in the first longitudinal direction X1 toward the housing 60. As the lumen end 71 of the catheter 70 moves toward the housing 60, the locking member 40 also advances toward the housing 60. The lumen end 71 of the catheter 70 is urged into the pathway 62 of the housing 60 and the upper surface 41a of the locking member 40 is urged into contact with the second longitudinal end 67 of the housing 60.

Figure 2:
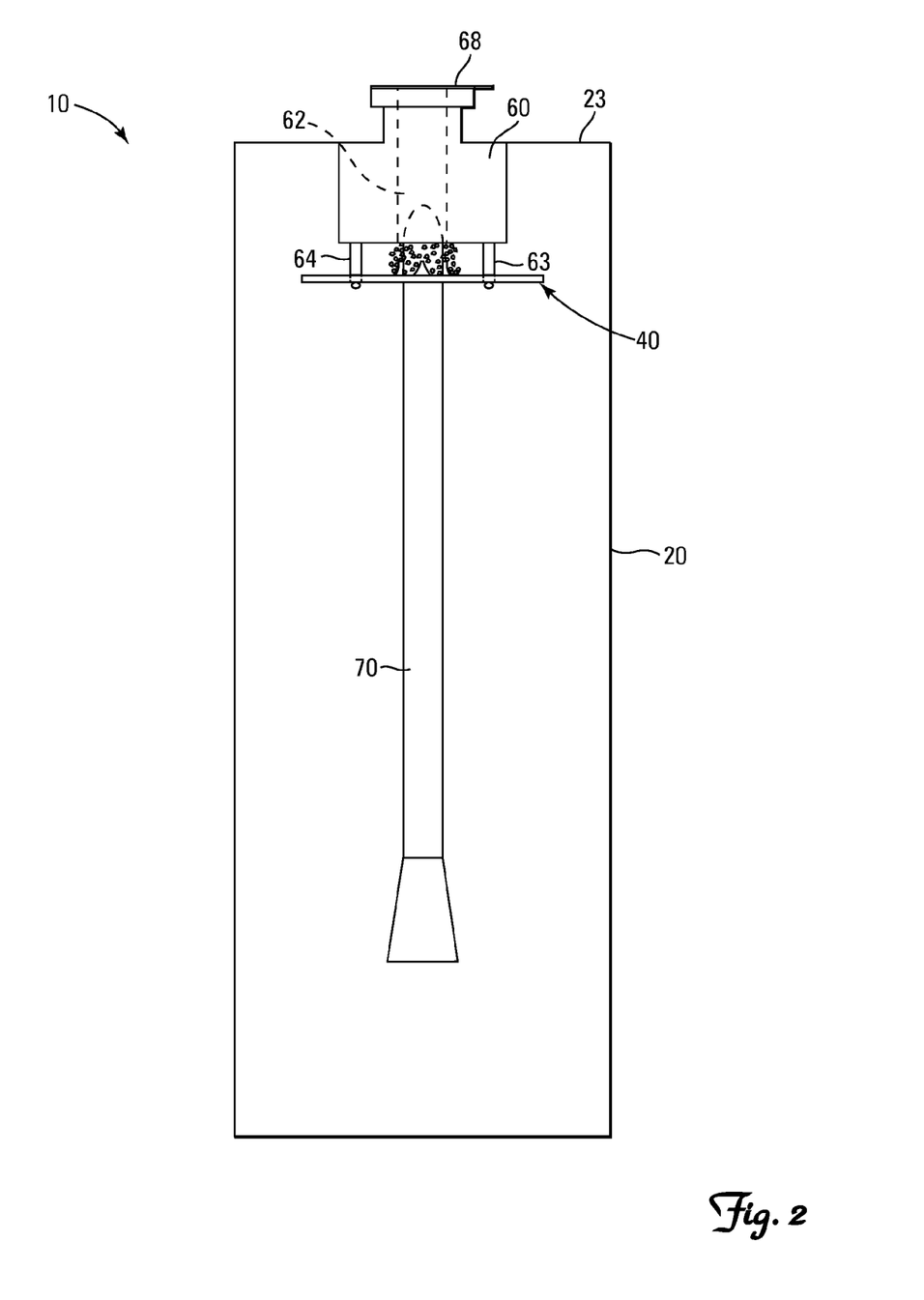
FIG. 2 is a front plan view of the invention in FIG. 1 shown with the catheter moving in the first longitudinal direction as the user advances the catheter into the exit of the package.
Figure 3:
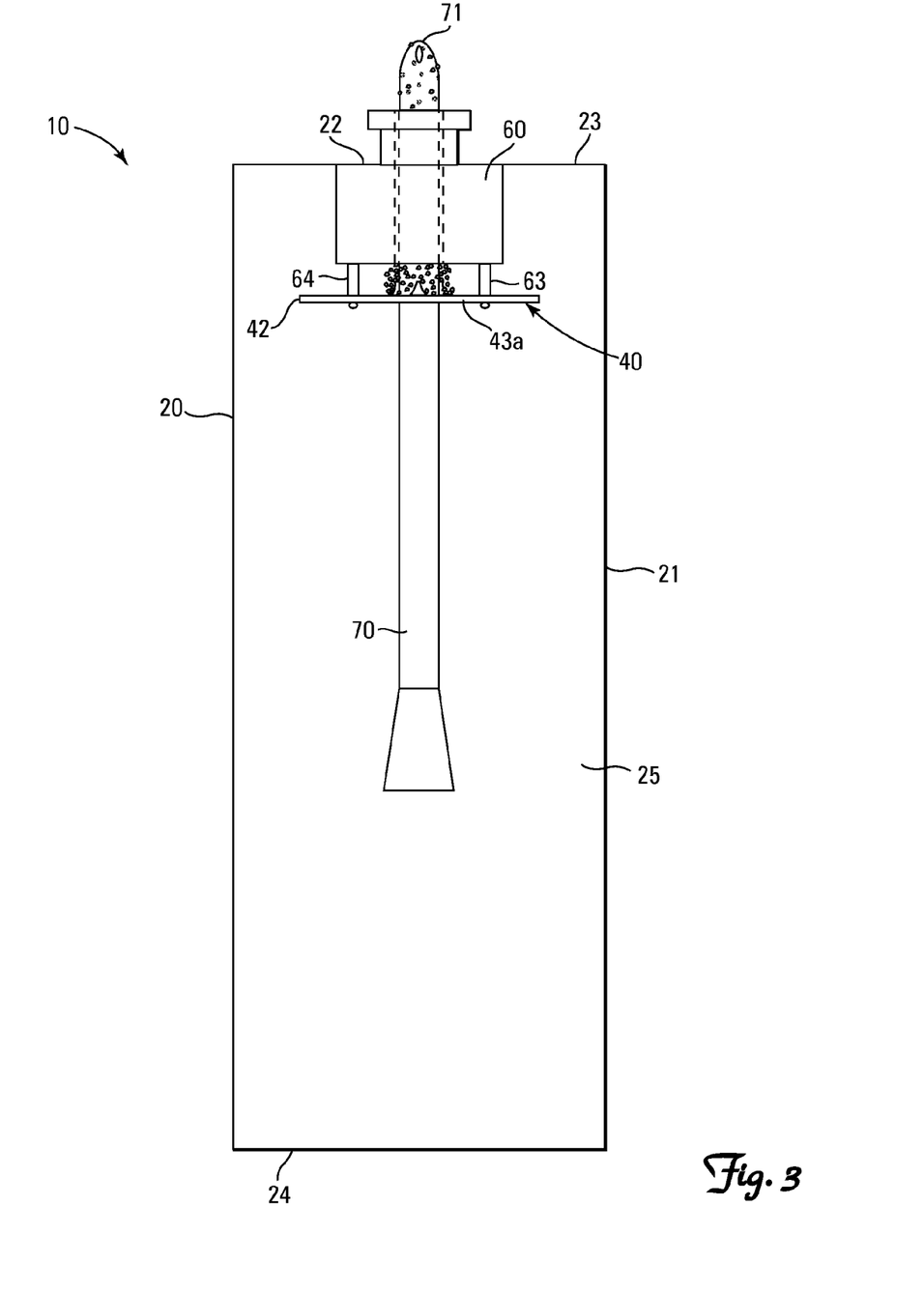
FIG. 3 is a front plan view of the invention in FIG. 3 with the movement control device engaging the housing to prevent movement in the second longitudinal direction.
Figure 4:
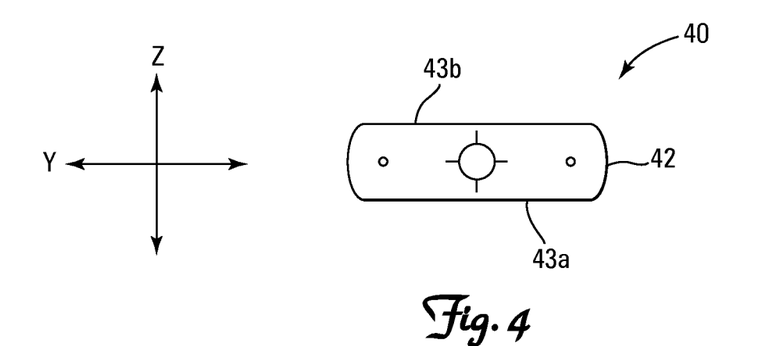
FIG. 4 is a top plan view of the monolithic planar locking member shown in FIG. 1.

In the embodiment of the invention shown in FIGS. 1-3, the housing 60 has first and second longitudinally extending engagement members 63 and 64 extending in the second longitudinal direction X2 from the housing 60. The engagement members 63 and 64 snap fit into locking orifices 44 in the locking member 40 preventing the locking member 40 from moving out of contact with the housing 60 member. In the embodiment of the invention shown in FIGS. 7 and 8, the housing 60 has slots or catches 65 in the second longitudinal end 67. The locking member 40 has snap fit latches 45 extending in the first longitudinal direction X1 on the first and second lateral ends 42 that are configured and arranged to mate with the slots or catches 65 in the housing 60. In both embodiments the catheter 70 and the locking member 40 are advanced in the first longitudinal direction X1. The lumen end 71 of the catheter 70 enters the pathway 62 to advance out of the package 20 and the locking member 40 snap fits into place with the housing 60.

Once the locking member 40 has snap fit into place with the housing 60, the locking member 40 can no longer move in the second longitudinal direction X2. The catheter 70 continues to advance out of the package 20 and into the urethra of the user. As the catheter 70 is advanced if it encounters resistance advancing in the first longitudinal direction X1, the one-way valve 50 in the locking member 40 grabs the catheter 70 and prevents it from moving in the second longitudinal direction X2.

In all of the embodiments, the locking member 40 prevents the funnel end 72 of the catheter 70 from advancing out of the package 20. This allows the package 20 to be used as a drainage vessel or an extended drainage tube if the second longitudinal end 24 of the package 20 was removed. It also allows the user to manipulate the catheter 70 without touching the catheter 70. This helps to prevent contamination of the catheter 70 and reduces the mess to the hands of the user.

I claim:

1. An intermittent urinary catheter package, comprising:
   (a) a longitudinally extending flexible package configured to at least partially contain a catheter in a receiving chamber; and
   (b) a catheter movement control device disposed within the package and having (i) a monolithic planar locking member having longitudinally spaced upper and lower surfaces, laterally spaced ends, and transversely spaced front and back edges, and (ii) a one-way valve disposed through the upper and lower surfaces of the locking member and configured for receipt of the catheter and permitting advance of the catheter through the locking member in a first longitudinal direction but resisting return of an advanced catheter in a second longitudinal direction opposite the first longitudinal direction, wherein the catheter movement control device is configured to be manipulated from outside the package for disengaging the one-way valve to allow return of an advanced catheter in the second longitudinal direction.

2. The intermittent urinary catheter package, as set forth in claim 1, wherein at least one of the transversely spaced edges is attached to a longitudinally extending side of the package.

3. The intermittent urinary catheter package, as set forth in claim 2, wherein the at least one transversely spaced edges of the locking member is hingedly attached to the longitudinally extending side of the package.

4. The intermittent urinary catheter package, as set forth in claim 1, wherein the one way valve is a tricuspid valve or a quadricuspid valve.

5. The intermittent urinary catheter package, as set forth in claim 1, further comprising a catheter housing attached to a at least one longitudinally extending side of the package and having a longitudinal axis and defining a longitudinally extending pathway through the housing configured for receipt of the catheter and disposed a longitudinal distance from the valve in the first longitudinal direction.

6. The intermittent urinary catheter package, as set forth in claim 5, wherein the housing is positioned within an exit to the package.

* * * * *